United States Patent
Crescentini et al.

(10) Patent No.: US 10,571,531 B2
(45) Date of Patent: *Feb. 25, 2020

(54) HALL SENSOR AND SENSING METHOD, AND CORRESPONDING DEVICE

(71) Applicant: STMicroelectronics S.r.l., Agrate Brianza (IT)

(72) Inventors: Marco Crescentini, Vallefoglia (IT); Marco Tartagni, Meldola (IT); Aldo Romani, Rimini (IT); Roberto Canegallo, Rimini (IT); Marco Marchesi, Borgonovo V.T. (IT); Domenico Cristaudo, Tremestieri Etneo (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/918,809

(22) Filed: Mar. 12, 2018

(65) Prior Publication Data

US 2018/0203076 A1 Jul. 19, 2018

Related U.S. Application Data

(63) Continuation of application No. 15/142,270, filed on Apr. 29, 2016, now Pat. No. 9,952,291.

(30) Foreign Application Priority Data

Jul. 28, 2015 (IT) .................. 102015000039150

(51) Int. Cl.
*G01R 33/06* (2006.01)
*G01R 33/07* (2006.01)
(Continued)

(52) U.S. Cl.
CPC .......... *G01R 33/075* (2013.01); *B64G 1/366* (2013.01); *G01R 33/0029* (2013.01);
(Continued)

(58) Field of Classification Search
CPC .. B64G 1/366; G01R 33/0206; G01R 33/028; G01R 33/038; G01R 33/1215;
(Continued)

(56) References Cited

U.S. PATENT DOCUMENTS 6,008,643 A 12/1999 Mani et al.
6,433,535 B1 8/2002 Marx et al.
(Continued)

FOREIGN PATENT DOCUMENTS

| CN | 205691141 U | 11/2016 |
|---|---|---|
| DE | 19839446 A1 | 3/2000 |
| EP | 2490036 A1 | 8/2012 |

OTHER PUBLICATIONS

Marchesi, M., et al., "A 2 MS/s 10A Hall Current Sensor SoC with Digital Compressive Sensing Encoder in 0.16 nm BCD", STMicroelectronics, Italy, IEEE 2016, pp. 393-396.
(Continued)

*Primary Examiner* — Raul J Rios Russo
(74) *Attorney, Agent, or Firm* — Slater Matsil, LLP

(57) ABSTRACT

A Hall sensor may include a Hall sensing element configured to produce a Hall voltage indicative of a magnetic field when traversed by an electric current, and a first pair of bias electrodes mutually opposed in a first direction across the Hall sensing element. The Hall sensor may include a second pair of bias electrodes mutually opposed in a second direction across the Hall sensing element. The Hall sensor may include a first pair of sensing electrodes mutually opposed in a third direction across the Hall sensing element, and a second pair of sensing electrodes mutually opposed in a
(Continued)

fourth direction across the Hall sensing element. The fourth direction may be orthogonal to the third direction, each sensing electrode being between a bias electrode of the first pair and a bias electrode of the second pair.

24 Claims, 3 Drawing Sheets

(51) Int. Cl.

| | | |
|---|---|---|
| *G01R 33/038* | (2006.01) | |
| *G01R 33/028* | (2006.01) | |
| *G01R 33/02* | (2006.01) | |
| *G01R 33/00* | (2006.01) | |
| *B64G 1/36* | (2006.01) | |
| *G01R 15/20* | (2006.01) | |
| *G01R 33/12* | (2006.01) | |
| *G01N 27/90* | (2006.01) | |
| *G11C 19/08* | (2006.01) | |
| *H01F 7/02* | (2006.01) | |

(52) U.S. Cl.
CPC ....... *G01R 33/0206* (2013.01); *G01R 33/028* (2013.01); *G01R 33/038* (2013.01); *G01R 33/07* (2013.01); *G01N 27/90* (2013.01); *G01R 15/20* (2013.01); *G01R 33/0283* (2013.01); *G01R 33/1215* (2013.01); *G11C 19/085* (2013.01); *H01F 7/0273* (2013.01)

(58) Field of Classification Search
CPC .... G01R 15/20; G01R 33/0283; G01R 33/38; G01N 27/90; G11C 19/085; H01F 7/0273
USPC ... 324/51, 55, 117, 127, 200, 227, 228, 244, 324/251
See application file for complete search history.

(56) References Cited

U.S. PATENT DOCUMENTS

| | | |
|---|---|---|
| 8,466,526 B2 | 6/2013 | Hioka et al. |
| 9,217,783 B2 | 12/2015 | Kolb et al. |
| 2007/0090825 A1* | 4/2007 | Shoji .................... G01R 15/205 324/117 R |
| 2008/0238410 A1 | 10/2008 | Charlier et al. |
| 2009/0121707 A1 | 5/2009 | Schott |
| 2009/0201017 A1* | 8/2009 | Peev .................. G01R 33/0005 324/251 |
| 2010/0021982 A1 | 9/2010 | Rocznik et al. |
| 2012/0133356 A1* | 5/2012 | Charlier ............. G01R 33/0017 324/202 |
| 2012/0210800 A1 | 8/2012 | Huber et al. |
| 2013/0009659 A1* | 1/2013 | Liu ........................ G01R 35/00 324/756.02 |
| 2013/0300402 A1* | 11/2013 | Liu ......................... G01R 33/09 324/202 |
| 2014/0070795 A1 | 3/2014 | Kolb et al. |
| 2015/0219689 A1* | 8/2015 | Liu ........................ G01R 35/00 324/202 |
| 2017/0030983 A1 | 2/2017 | Crescentini et al. |

OTHER PUBLICATIONS

Bilotti et al., "Monolithic Magnetic Hall Sensor Using Dynamic Quadrature Offset Cancellation", IEEE Journal of Solid-State Circuits, vol. 32, No. 6, Jun. 1997, pp. 829-836.

Banjevic et al, "2D CMOS Integrated Mangetometer Based on the Miniaturized Circular Vertical Hall Device", Transducers 2009, Denver, CO, Jun. 21-25, 2009, pp. 877-880.

Jiang et al, "A Continuous-Time Ripple Reduction Technique for Spinning-Current Hall Sensors", IEEE Journal of Solid-State Circuits, vol. 49, No. 7, Jul. 2014, pp. 1525-1534.

* cited by examiner

HALL SENSOR AND SENSING METHOD, AND CORRESPONDING DEVICE

CROSS-REFERENCE TO RELATED APPLICATIONS

This application is a continuation of U.S. application Ser. No. 15/142,270, filed on Apr. 29, 2016, which claims priority to Italian Application No. 102015000039150, filed on Jul. 28, 2015, which applications are hereby incorporated herein by reference.

TECHNICAL FIELD

The present disclosure relates to sensors devices, and more particularly to Hall sensors and related methods.

BACKGROUND

The increased interest for high-speed (e.g., 1 MHz bandwidth) Hall sensors adapted for use in applications, such as lossless current sensing, is confronted by intrinsic limitations due to, for example, the capacitive load of switches and circuit complexity (e.g., double feedback loop with analog-to-digital (ADC)/digital-to-analog (DAC) conversion in the loop). It may be helpful to have an alternative Hall sensor system.

SUMMARY

Generally speaking, a Hall sensor may include a Hall sensing element configured to produce a Hall voltage indicative of a magnetic field when traversed by an electric current, and a first pair of bias electrodes mutually opposed in a first direction across the Hall sensing element. The Hall sensor may include a second pair of bias electrodes mutually opposed in a second direction across the Hall sensing element, the second direction being orthogonal to the first direction. The Hall sensor may include a first pair of sensing electrodes mutually opposed in a third direction across the Hall sensing element, and a second pair of sensing electrodes mutually opposed in a fourth direction across the Hall sensing element. The fourth direction may be orthogonal to the third direction, each sensing electrode being between a bias electrode of the first pair and a bias electrode of the second pair.

DETAILED DESCRIPTION OF ILLUSTRATIVE EMBODIMENTS

In the ensuing description one or more specific details are illustrated, aimed at providing an in-depth understanding of examples of embodiments. The embodiments may be obtained without one or more of the specific details, or with other methods, components, materials, etc. In other cases, known structures, materials, or operations are not illustrated or described in detail so that certain aspects of embodiments will not be obscured.

Reference to "an embodiment" or "one embodiment" in the framework of the present description is intended to indicate that a particular configuration, structure, or characteristic described in relation to the embodiment is comprised in at least one embodiment. Hence, phrases such as "in an embodiment" or "in one embodiment" that may be present in one or more points of the present description do not necessarily refer to one and the same embodiment. Moreover, particular conformations, structures, or characteristics may be combined in any adequate way in one or more embodiments. The references used herein are provided merely for convenience and hence do not define the scope of protection or the scope of the embodiments.

One or more embodiments may apply to high-bandwidth Hall sensor systems for use in the automotive sector and other industrial applications (e.g. speed detection, lossless current sensing, and so on). According to one or more embodiments, such an object is achieved by way of a Hall sensor having the features set forth in the following. One or more embodiments may also relate to a corresponding sensing method and device. One or more embodiments may implement a "spinning" current scheme, for example, in order to reduce offset.

One or more embodiments may include, for example, an octagonal Hall sensing element with separated contacts wherein sensing signal readout may be on two channels that acquire Hall voltages in two orthogonal directions. In one or more embodiments, an analog output may be digitized with data compressed by a compressive sensing algorithm.

One or more embodiments may offer one or more of the following advantages: high bandwidth lossless current sensing made possible, for example, up to 1 MHz, rejection of the earth magnetic field, compressive sensing of measured data, sensing by way of a regulated current mirror to achieve a high voltage drop on the sensor, an analog readout circuit including two symmetrical channels may acquire Hall voltages in two perpendicular directions with auto-zeroing of op-amp offset, and small offset-induced ripples at the spinning frequency. One or more embodiments may provide the capability of dynamically changing the acquisition bandwidth (e.g., B) with the frequency fck of an external clock, for example, with B=fck/32.

Figure 1:
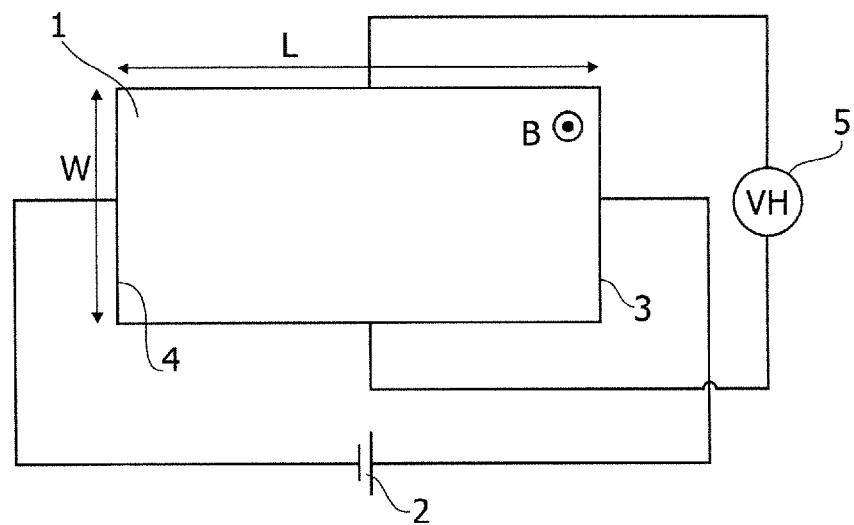
FIG. 1 is a schematic diagram of Hall effect sensing, according to the present disclosure.

In FIG. 1, reference 1 denotes a planar Hall sensing element of, for example, a thickness t which may include a semiconductor material including, for example, an N-type doped region serving as a Hall sensing portion proper superposed over a P-type, lightly-doped region. A voltage Vdd from a source 2 applied between two bias electrodes 3, 4 arranged parallel to each other at a distance L may cause a bias current to flow across a sensing element 1 having a width W.

In the presence of an applied magnetic field B transverse to the planar sensing element 1, a Hall voltage VH may be sensed across the sensing element 1 transversally to the direction of a flow of the bias current IBIAS between the bias electrodes 3 and 4 which is indicative of the intensity of the magnetic field B, for example, with VH proportional to RH B IBIAS /t, where RH is known as the Hall resistance. The basic principles of operation of Hall sensors are otherwise known by the person of ordinary skill in the art, which makes it unnecessary to provide more detailed description herein. Various implementations may expand over the basic principle summarized in the foregoing by resorting, for example, to "spinning" arrangements in order to counter drawbacks such as offset voltages and/or ripple which may arise during operation of a Hall sensor. Exemplary of such implementations are, for example: A. Bilotti et al: "Monolithic Magnetic Hall Sensor Using Dynamic Quadrature Offset Cancellation", IEEE Journal of Solid-State Circuits, Vol.32, No.6, June 1997, pp. 829-835; J. Jiang et al: "A Continuous-Time Ripple Reduction Technique for Spinning-Current Hall Sensors", IEEE Journal of Solid-State Circuits, Vol.49, No.7, July 2014, pp. 1525-1533; and U.S. Pat. No. 8,466,526 to Hioka et al.

One or more embodiments as exemplified in FIGS. 2 to 6 may include a planar Hall sensing element 10 adapted to be exposed to a (transverse) magnetic field B and including a material (e.g., semiconductor material) producing a Hall voltage indicative of the intensity of magnetic field when traversed by an electric current. The general principles of operation of such a sensing element have been discussed previously in connection with FIG. 1.

In one or more embodiments, the planar sensing element 10 may have provided thereon (by typical methods) a set of bias electrodes B1, B2, B3, B4 and a set of sensing electrodes S1, S2, S3, S4. In one or more embodiments, the sensing element 10 may have an octagonal shape overall. It will be otherwise appreciated that such a shape, while optional, is not mandatory.

In one or more embodiments, an arrangement of bias electrodes may include a first pair of bias electrodes B1, B2 mutually opposed in a first direction D1 across the sensing element 10, and a second pair of bias electrodes B3, B4, mutually opposed in a second direction D2 across the sensing element 10 with the second direction D2 orthogonal to the first direction D1, so that the bias electrodes B1, B2, B3, B4 are arranged, so-to-say, according to a cross-like pattern. In some embodiments, an arrangement of sensing electrodes may include a first pair of sensing electrodes S1, S3 mutually opposed in a third direction D3 across the sensing element 10, and a second pair of sensing electrodes S2, S4 mutually opposed in a fourth direction D4 across the sensing element 10, with the fourth direction D4 orthogonal to the third direction D3.

Figure 2:
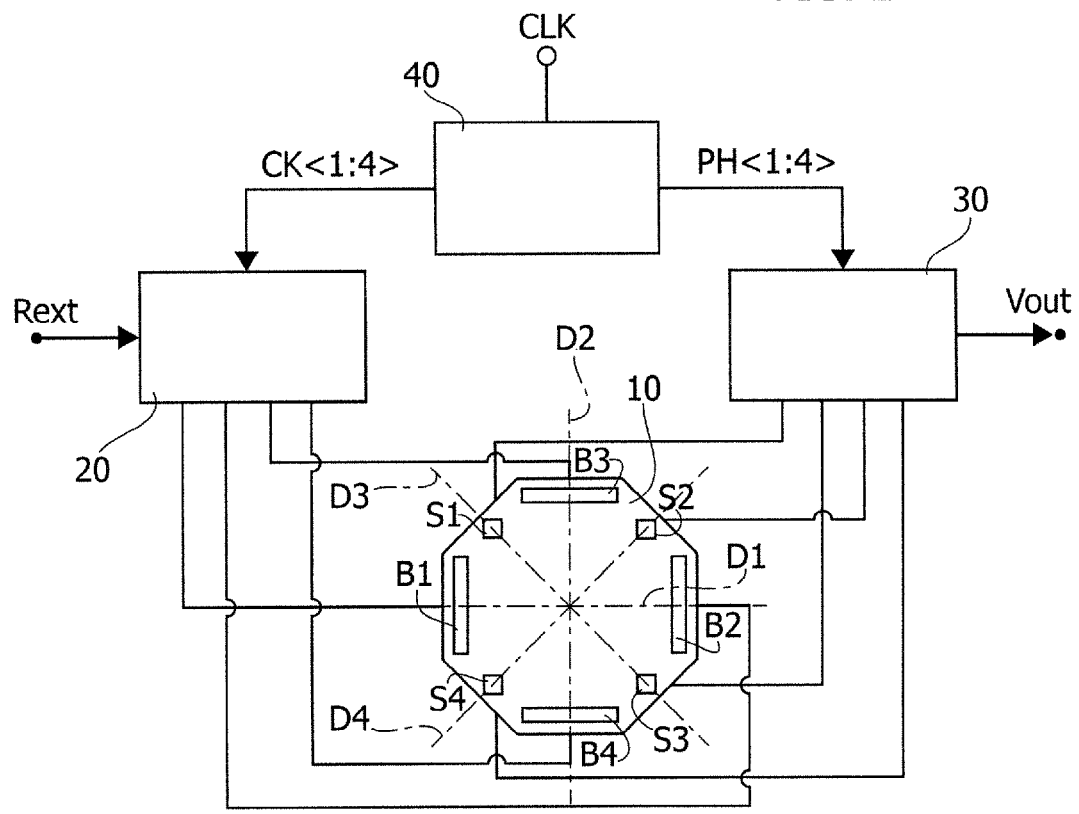
FIG. 2 is a schematic diagram of a Hall sensor, according to the present disclosure.
Figure 3:
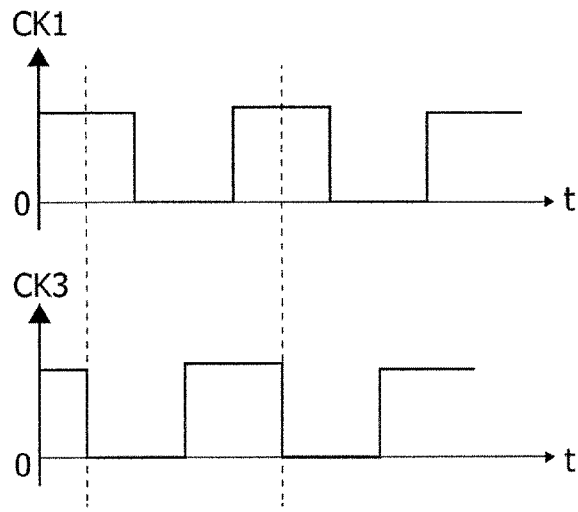
FIG. 3 is a timing diagram for the Hall sensor, according to the present disclosure.

Similarly to the bias electrodes B1 to B4, the sensing electrodes S1 to S4 may thus be arranged according to a cross-like pattern. As seen in FIG. 2, where the directions D1 to D4 are expressly indicated (these are not represented in the other figures for the sake of simplicity), the third and fourth directions D3, D4 are rotated 45° with respect to the first and second directions D1, D2. Consequently, in one or more embodiments, each one of the sensing electrodes S1 to S4 may be arranged between a bias electrode of the first pair B1, B2 and a bias electrode of the second pair B2, B4.

For instance, in some embodiments, the sensing electrode S1 may be arranged between the bias electrode B1 (first pair) and the bias electrode B3 (second pair); the sensing electrode S2 may be arranged between the bias electrode B3 (second pair) and the bias electrode B2 (first pair); the sensing electrode S3 may be arranged between the bias electrode B2 (first pair) and the bias electrode B4 (second pair); and the sensing electrode S4 may be arranged between the bias electrode B1 (first pair) and the bias electrode B4 (second pair). In one or more embodiments, the bias electrodes B1 to B4 are bar-like electrodes with the bias electrodes in the first pair B1, B2 extending parallel to each other. This may also apply to the bias electrodes B3 and B4 in the second pair which may again be bar-like and extend parallel to each other.

In some embodiments, the sensing element 10 may be coupled to a bias module 20 configured to provide (as better detailed in the following) bias currents between the electrodes B1, B2 of the first pair and between the bias electrodes B3, B4 of the second pair. The sensor may also include a readout module 30 which (again as better detailed in the following) is configured to read the Hall voltages produced between the sensing electrodes of the first pair (S1, S3) and the sensing electrodes of the second pair (S2, S4). In one or more embodiments, the bias module 20 may be driven by an external reference signal Rext. In some embodiments, the readout module 20 may produce an output sensing signal Vout. In one or more embodiments, a phase generator 40 may be provided coupled to the bias module 20 and the readout module 30 for producing mutually time-phased operation (that is, time-coordinated operation) of the bias module 20 and readout module 30. In some embodiments this may involve, for example, first, second, third and fourth biasing phases CK<1:4>mutually coordinated with first, second, third and fourth sensing (that is readout) phases PH<1:4>.

As better detailed in the following, in one or more embodiments, the bias module 20 may be configured to selectively vary the direction of the bias currents between the bias electrodes of the first pair B1, B2 and the bias electrodes of the second pair B3, B4. In other words, a bias current may flow in a first direction from electrode B1 to electrode B2 and also in a second, opposed direction from electrode B2 to electrode B1. Similarly, a bias current may flow in a first direction from electrode B3 to electrode B4 and also in a second, opposed direction from electrode B4 to electrode B3.

In some embodiments, the phase generator 40 may be driven by a clock signal CLK, for example, derived from a system clock generator of the electronic device including a Hall sensor as exemplified herein. In one or more embodiments, the phase generator 40 may generate mutually phased drive signals for the bias module 20 and readout module 30, respectively. In some embodiments, these drive signals may include square-wave signals CK1, CK3 with a 50% duty cycle, the signals CK1, CK3 being "in quadrature", that is 90° offset, to each other.

The clock signals CK1, CK3 may be used to generate within the bias module 20 a set of drive signals CK1, CK2, CK3, CK4 with CK2 being the logic complementary of CK1 (that is CK1neg) and CK4 the logic complementary of CK3 (that is CK3neg). The drive signals CK1, CK2, CK3, CK4 may be applied to a set of switches 61, 62, 63, 64 (e.g. electronic switches such as MOSFETs) arranged according to the exemplary configuration shown in FIG. 5 so that bias currents as provided by a current generator 65, possibly controlled via an input Rext, may be caused to flow between the electrodes B1, B2 (first pair) and B3, B4 (second pair). In one or more embodiments, the current generator 65 may be a solid-state current generator (e.g. a current mirror or current generator) adapted to operate at a supply voltage Vdd. In some embodiments, the eight switches 61, 62, 63, 64 may be assumed to be "on" (that is conductive) when the corresponding drive signal (CK1, CK2, CK3, CK4 as shown in FIG. 5) is "high" and then "off" (that is non-conductive) when the respective drive signal CK1, CK2, CK3, CK4 is "low".

Figure 5:
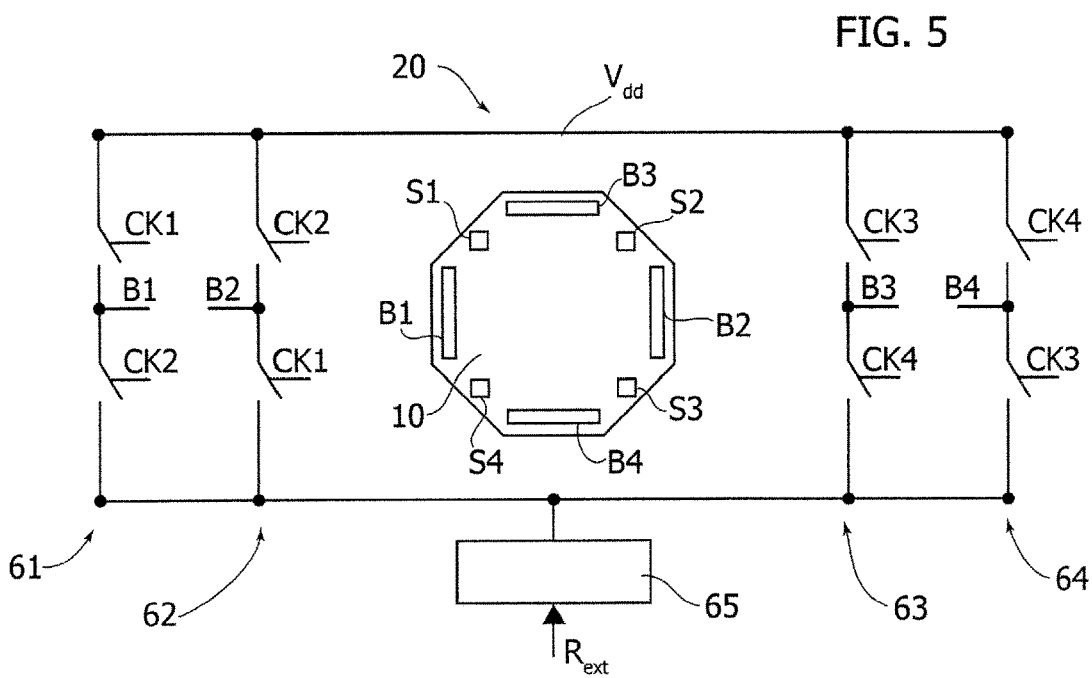
FIG. 5 is a schematic diagram of bias current generation, according to the present disclosure.

In the exemplary configuration of FIG. 5, the switches 61, 62, 63, 64 are arranged in a sort of "full-bridge" arrangement so that the direction of flow of the bias currents between the electrodes B1, B2 and B3, B4 may be reversed as a function of the logic values ("high" or "low") of CK1, CK2, CK3, CK4. In one or more embodiments, such an arrangement may permit to implement (in a cyclical manner) four biasing phases CK<1:4>according to the following pattern: in a first biasing phase (phase 1) CK1 and CK4 are high, and CK2 and CK3 are low, so that bias currents from the generator 65 will flow from contact B1 to contact B2 and from contact B4 to contact B3; in a second biasing phase (phase 2) CK1 is still high with CK2 is still low, CK4 toggles to low while CK3 toggles to high; therefore, a bias current will keep on flowing from B1 to B2 as before, while the direction of the bias current between the electrodes of the second pair will be changed, with the current now flowing from B3 to B4; in a subsequent third biasing phase (phase 3) CK2 and CK3 are high, while CK1 and CK4 are low; a bias current will keep on flowing from B3 to B4 as before, while the direction of the bias current between the electrodes of the first pair will be changed, with the current now flowing from B2 to B1; finally, during a fourth biasing phase (phase 4) CK2 and CK4 are high, while CK1 and CK3 are low and the current will flow from B2 to B1 and from B4 to B3.

Figure 4:
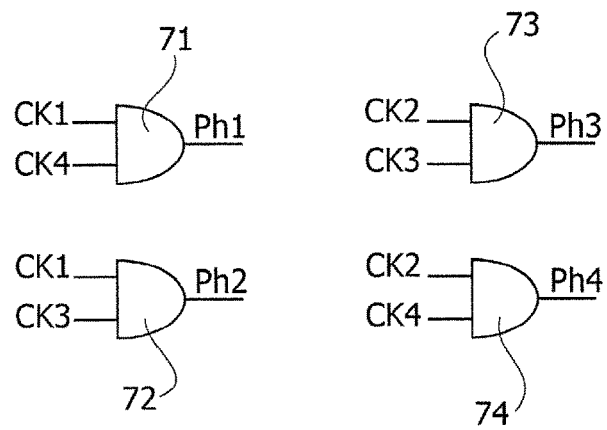
FIG. 4 is a schematic diagram of timing (phasing) signal generation, according to the present disclosure.

More generally, during the first, second, third and fourth biasing phases as discussed previously: the bias current between the bias electrodes in the first pair (i.e., B1, B2) will be in one direction during the first and second biasing phases and in the opposed direction in the third and fourth biasing phases; and the bias current between the bias electrodes of the second pair (i.e., B3 and B4) will be in one direction in the first and fourth biasing phases and in the opposed direction in the second and third biasing phases. FIG. 4 is exemplary of a simple combinatory network including four logical product (AND gates) 71, 72, 73, 74 adapted to be fed with the signals CK1, CK2, CK3, CK4 to generate four clocking signals Ph1, Ph2, Ph3, Ph4 adapted to operate corresponding switches 81 to 86 in the readout module 30, as in FIG. 6.

Figure 6:
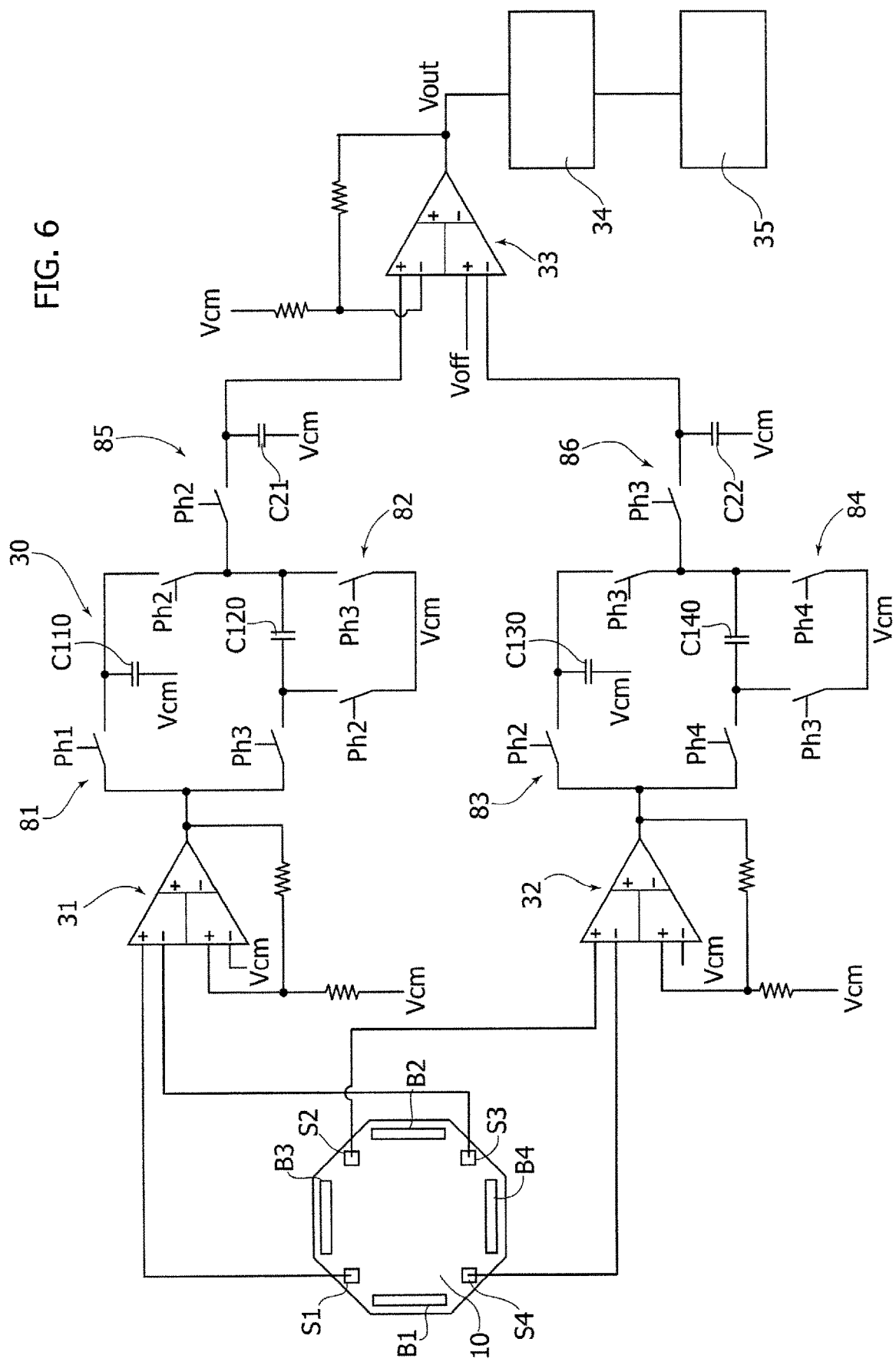
FIG. 6 is a schematic diagram of signal sensing, according to the present disclosure.

It will be otherwise appreciated that while represented as independent modules for the sake of simplicity in the schematic diagram of FIG. 2, the bias module 20, the readout module 30 and the phase generator 40 may be de facto incorporated to a single circuit adapted to produce (in a manner known per se) the drive signals Ck1 to Ck4 for the switches 61 to 64 of FIG. 5 as well as the drive signals Ph1 to Ph4 for the switches 81 to 86 of FIG. 6. Specific application requirements may dictate options for differently dividing these various circuit elements. In some embodiments, the readout module 30 may include first and second detectors 31 and 32 to, for example, differentially sense the Hall voltages between the sensing electrodes S1, S3 of the first pair (differential detector 31) and between the sensing electrodes S2, S4 of the second pair (differential detector 32).

In one or more embodiments, the differential detectors 31, 32 may include differential difference amplifiers (DDA) including, in addition to the differential stage fed with the Hall voltages from the sensing electrodes S1, S3 (first pair) and S2, S4 (second pair) also a second differential stage closing the differential feedback with respect to a stable common mode voltage Vcm. In some embodiments, the differential detectors (e.g. DDA) 31, 32 may include an output non-inverting amplifier amplifying the input differential voltage (e.g. by 25) and outputting a single ended voltage. The input DDA may exhibit a high gain, for example, in order to reduce noise as usual offset, optionally together with a fast settling behavior.

In one or more embodiments, the outputs from the differential detectors 31, 32 may be fed to an, for example, switched capacitor circuit including two capacitors C110, C120 for the first sensing channel including the differential detector 31 and two capacitors C130, C140 for the second sensing channel including the differential detector 32. In some embodiments, the switched capacitor circuits in question may be intended to subtract from each other the Hall voltages of opposed polarities sensed between the sensing electrodes of the first pair S1, S3, and the sensing electrodes of the second pair S2, S4 when the direction of the currents between the bias electrodes B1, B2 (first pair) and B3, B4 (second pair) is reversed as indicated previously. The voltages obtained by subtracting from each other these Hall voltages of opposed polarities may then be capacitively stored on second capacitors C21 (first channel) and C22 (second channel).

Once again, in one or more embodiments, the switches 81, 82, 83, 84, 85, 86 (e.g. electronic switches such as MOSFETs) may be assumed to be "on" (that is conductive) when the corresponding drive signal (Ph1, Ph2, Ph3, Ph4 as shown in FIG. 6) is "high" and "off" (that is non-conductive) when the respective drive signal Ph1, Ph2, Ph3, Ph4 is "low". In some embodiments, the sensing voltages produced by the two sensing channels including the detectors 31 and 32 may be fed to a further non-inverting amplifier stage 33 which may amplify the input differential voltage for a certain gain, for example, outputting a single-ended output voltage Vout. This may again be a differential difference amplifier (DDA).

In one or more embodiments, the output voltage Vout may be subjected to sample and hold (S&H) processing at 34 and to analog-to-digital conversion optionally followed by digital compression at 35. In one or more embodiments, a single input of the amplifier 33 may be an external adjustable voltage compensating for the offset introduced by the amplifier 33, while the common mode voltage Vcm is used to set the DC common mode biasing to half the voltage supply.

Time-phased operation of the bias module 20 and readout module 30 as exemplified in FIG. 2 may involve first, second, third and fourth sensing phases related (that is, time-coordinated) with the first, second, third, and fourth biasing phases considered in the foregoing. In some embodiments, the respective bias and sensing phases may thus coincide, so that, for example, during the "joint" phase i a bias current may flow into B1 e B4 with sensing between S1 and S3. This may involve, for example, CK1=CK4=PH1=1 with all the other signals equal to 0, with the subsequent phases corresponding to a sort of clockwise "spinning".

For the sake of simplicity, such a first phase may be considered as a starting point in illustrating a possible cyclical sequence of sensing phases. During that phase, the first sensing channel (including the differential detector 31 may amplify the input differential voltage between the sensing electrodes S1, S3 of the first pair by saving such a voltage on the capacitor C110. During a subsequent second sensing phase, the first sensing channel including the detector 31 may saturate while the second sensing channel (including the differential detector 32) may amplify the input signal between the sensing electrodes S2, S4 of the second pair and save these on the capacitor C130. In a further subsequent third phase, the token may go back to the first sensing channel (including the first differential detector 31), by taking into account that at this point the polarity of the input voltage sensed between the electrodes S1, S3 will be reversed due to the reversal of the direction of the current between the bias electrodes B1, B2). Such a voltage may be stored on capacitor C120, with the difference between the voltages stored on capacitors C110 and C120 adapted to be transferred (via switch 85) onto capacitor C21 to be capacitively stored thereon.

The second sensing channel, including the differential detector 32, may operate during a (due to the cyclical pattern of the sensing phases) fourth sensing phase in the same manner just described for the first sensing channel including the differential detector 31 during the third phase discussed previously, for example, with the result of subtraction of the voltages stored on the capacitors C130 and C140 transferred and capacitively stored on the capacitor C22. The difference of the voltages stored on the capacitors C21 and C22 may be sampled, subtracted and amplified by the amplifier stage 33 having a gain of, for example, 4. It will be appreciated that the switched capacitor circuits considered herein may also have the effect of auto-zeroing the offset of the input differential detectors 31, 32: in fact the offset of such a differential detectors does not change polarity in different phases. The sensor offset may be cancelled out by orthogonal measurements that is by the subtraction of the outputs from the first detection channel (including differential detector 31) and the second sensing channel (including the differential detector 32).

One or more embodiments may significantly reduce offset-induced ripples that appear at the "spinning" frequency: some embodiments may achieve that result by operating synchronously with the spinning frequency (which may be dictated by the frequency of the clock signal CLK—see FIG. 2). Also, it will be appreciated that operation as exemplified in the foregoing may be independent of the actual directions of bias current flowing between the bias electrodes of the first pair B1, B2 and a second pair B3, B4 provided such directions are changed as considered previously so that a corresponding change of the polarity of the sensing voltages may be produced. That is, while the previous discussion it has been assumed that during the first and second biasing phases (phase 0, phase 1) the current flows, for example, from electrode B1 to electrode B2, operation will not be adversely affected if, during the same phases, current were to flow from electrode B2 to electrode B1, the foregoing applying also to the bias current flowing between electrodes B1 and B4.

Without prejudice to the underlying principles, the details and embodiments may vary, even significantly, with respect to what has been described by way of example only without departing from the extent of protection. The extent of protection is defined by the annexed claims.

What is claimed is:

1. A Hall sensor comprising:
   a Hall sensing element configured to produce a Hall voltage indicative of a magnetic field when traversed by an electric current;
   a first pair of bias electrodes mutually opposed in a first direction across the Hall sensing element;
   a second pair of bias electrodes mutually opposed in a second direction across the Hall sensing element, the second direction being orthogonal to the first direction;
   a first pair of sensing electrodes mutually opposed in a third direction across the Hall sensing element, the third direction being different than the first and second directions; and
   a second pair of sensing electrodes mutually opposed in a fourth direction across the Hall sensing element, the fourth direction being orthogonal to the third direction.

2. The Hall sensor of claim 1, wherein the third and fourth directions are respectively angularly spaced by 45° from the first and second directions.

3. The Hall sensor of claim 1, wherein each bias electrode comprises a bar-shaped electrode, wherein the first pair of bias electrodes extends in parallel, and wherein the second pair of bias electrodes extends in parallel.

4. The Hall sensor of claim 1, further comprising:
   a bias module configured to selectively apply bias currents between the bias electrodes of the first pair and between the bias electrodes of the second pair; and
   a readout module configured to selectively sense Hall voltages between the sensing electrodes of the first pair and between the sensing electrodes of the second pair.

5. The Hall sensor of claim 4, further comprising a phase generator coupled with the bias module and the readout module, and configured to produce mutually time-phased operation of the bias module and the readout module.

6. The Hall sensor of claim 4, wherein the bias module is configured to selectively vary a direction of the bias currents between the bias electrodes of the first pair and between the bias electrodes of the second pair.

7. The Hall sensor of claim 4 wherein the readout module comprises first and second differential detectors configured to differentially sense the Hall voltages between the sensing electrodes of the first pair and between the sensing electrodes of the second pair.

8. The Hall sensor of claim 7, wherein the readout module comprises first and second subtraction units coupled to the first and second differential detectors and configured to subtract from each other the Hall voltages of opposed polarity sensed between the sensing electrodes of the first pair and between the sensing electrodes of the second pair.

9. The Hall sensor of claim 8, wherein the first and second subtraction units each comprises a switched-capacitor circuit.

10. The Hall sensor of claim 8, further comprising first and second capacitor circuits configured to store the Hall voltages obtained from the first and second subtraction units.

11. The Hall sensor of claim 10, further comprising a sample and hold circuit configured to sample the Hall voltages from the first and second capacitor circuits, and analog-to-digital circuits configured to convert the Hall voltages from the sample and hold circuit, and compress the Hall voltages.

12. A Hall sensor comprising:
   a Hall sensing element configured to produce a Hall voltage indicative of a magnetic field when traversed by an electric current;
   a first pair of bias electrodes mutually opposed in a first direction across the Hall sensing element;
   a second pair of bias electrodes mutually opposed in a second direction across the Hall sensing element, the second direction being different first direction;
   a first pair of sensing electrodes mutually opposed in a third direction across the Hall sensing element, the third direction different than the first and second directions; and
   a second pair of sensing electrodes mutually opposed in a fourth direction across the Hall sensing element, the fourth direction being different than the first, second and third directions, each sensing electrode being between a bias electrode of the first pair and a bias electrode of the second pair.

13. The Hall sensor of claim 12 wherein each bias electrode comprises a bar-shaped electrode, wherein the first pair of bias electrodes extends in parallel, and wherein the second pair of bias electrodes extends in parallel.

14. The Hall sensor of claim 12 further comprising:
a bias module configured to selectively apply bias currents between the bias electrodes of the first pair and between the bias electrodes of the second pair; and
a readout module configured to selectively sense Hall voltages between the sensing electrodes of the first pair and between the sensing electrodes of the second pair.

15. The Hall sensor of claim 14 further comprising a phase generator coupled with the bias module and the readout module, and configured to produce mutually time-phased operation of the bias module and the readout module.

16. The Hall sensor of claim 14 wherein the bias module is configured to selectively vary a direction of the bias currents between the bias electrodes of the first pair and between the bias electrodes of the second pair.

17. The Hall sensor of claim 14 wherein the readout module comprises first and second differential detectors configured to differentially sense the Hall voltages between the sensing electrodes of the first pair and between the sensing electrodes of the second pair.

18. The Hall sensor of claim 17 wherein the readout module comprises first and second subtraction units coupled to the first and second differential detectors and configured to subtract from each other the Hall voltages of opposed polarity sensed between the sensing electrodes of the first pair and between the sensing electrodes of the second pair, wherein the first and second subtraction units each comprises a switched-capacitor circuit, and wherein the Hall sensor further comprises a sample and hold circuit configured to sample the Hall voltages from first and second capacitor circuits, and analog-to-digital circuits configured to convert the Hall voltages from the sample and hold circuit, and compress the Hall voltages.

19. The Hall sensor of claim 17 wherein the readout module comprises first and second subtraction units coupled to the first and second differential detectors and configured to subtract from each other the Hall voltages of opposed polarity sensed between the sensing electrodes of the first pair and between the sensing electrodes of the second pair wherein the Hall sensor further comprises:
first and second capacitor circuits configured to store the Hall voltages obtained from the first and second subtraction units; and
a sample and hold circuit configured to sample the Hall voltages from the first and second capacitor circuits, and analog-to-digital circuits configured to convert the Hall voltages from the sample and hold circuit, and compress the Hall voltages.

20. A Hall sensor comprising:
a Hall sensing element configured to produce a Hall voltage indicative of a magnetic field when traversed by an electric current;
a first pair of bias electrodes mutually opposed in a first direction across the Hall sensing element;
a second pair of bias electrodes mutually opposed in a second direction across the Hall sensing element, the second direction being orthogonal to the first direction;
a first pair of sensing electrodes mutually opposed in a third direction across the Hall sensing element;
a second pair of sensing electrodes mutually opposed in a fourth direction across the Hall sensing element, the fourth direction being orthogonal to the third direction;
a bias module configured to selectively apply bias currents between the bias electrodes of the first pair and between the bias electrodes of the second pair;
a readout module configured to selectively sense Hall voltages between the sensing electrodes of the first pair and between the sensing electrodes of the second pair; and
a phase generator coupled with the bias module and the readout module, the phase generator configured to produce mutually time-phased operation of the bias module and the readout module.

21. The Hall sensor of claim 20, wherein each sensing electrode being between a bias electrode of the first pair and a bias electrode of the second pair.

22. The Hall sensor of claim 20 wherein the third and fourth directions are respectively angularly spaced by 45° from the first and second directions.

23. The Hall sensor of claim 20, wherein the third direction is different than the first and second directions.

24. The Hall sensor of claim 20 wherein the bias module is configured to selectively vary a direction of the bias currents between the bias electrodes of the first pair and between the bias electrodes of the second pair.

* * * * *